(12) United States Patent
Brown

(10) Patent No.: US 12,734,281 B2
(45) Date of Patent: Sep. 15, 2026

(54) CUPPING DEVICE, SYSTEM, AND FEATURES

(71) Applicant: Cynthia R. Brown, Chapel Hill, NC (US)

(72) Inventor: Cynthia R. Brown, Chapel Hill, NC (US)

( * ) Notice: Subject to any disclaimer, the term of this patent is extended or adjusted under 35 U.S.C. 154(b) by 0 days.

(21) Appl. No.: 18/020,294

(22) PCT Filed: Aug. 9, 2021

(86) PCT No.: PCT/US2021/045207

§ 371 (c)(1),
(2) Date: Feb. 8, 2023

(87) PCT Pub. No.: WO2022/035753

PCT Pub. Date: Feb. 17, 2022

(65) Prior Publication Data

US 2024/0009362 A1 Jan. 11, 2024

Related U.S. Application Data

(60) Provisional application No. 63/063,537, filed on Aug. 10, 2020.

(51) Int. Cl.
*A61M 1/08* (2006.01)
*A61H 9/00* (2006.01)
*A61H 23/02* (2006.01)

(52) U.S. Cl.
CPC ............... *A61M 1/08* (2013.01); *A61H 23/02* (2013.01); *A61H 2009/0064* (2013.01); *A61H 2201/5097* (2013.01); *A61M 2205/05* (2013.01)

(58) Field of Classification Search
CPC ................ A61M 1/08; A61M 2205/05; A61M 2205/106; A61M 2205/7536; A61H 23/02;

(Continued)

(56) References Cited

U.S. PATENT DOCUMENTS 1,630,115 A * 5/1927 Duprey .............. A61H 23/0263 601/74
2,189,116 A * 2/1940 Niemiec ................ A61H 9/005 601/6

(Continued)

FOREIGN PATENT DOCUMENTS

CN 106860928 A * 6/2017
CN 106977885 A * 7/2017 ............. C08G 63/12

(Continued)

OTHER PUBLICATIONS

Extended Search Report in counterpart European Application No. 21856508.3 dated Jul. 19, 2024, pp. 1-5.

(Continued)

*Primary Examiner* — Tu A Vo
*Assistant Examiner* — Kelsey E Baller
(74) *Attorney, Agent, or Firm* — Additon, Pendleton, and Witherspoon, P.A.

(57) ABSTRACT

A suction cup includes a body having a sidewall extending around an interior space and a rim extending around an opening to the interior space. At least a portion of the body is elastic and configured so that the body is capable of being squeezed to transition the body from an at-rest configuration to a partially-collapsed configuration, and elastically biased toward the at-rest configuration. The volume of the interior space of the body is greater in the at-rest configuration than in the partially-collapsed configuration. The rim is less stiff than a portion of the sidewall that is spaced apart from the rim. The relatively soft rim seeks to provide optimal adhesion to the skin of a user, fortification of another portion the body of the cup seeks to better maintain its shape for enhanced ease of use, and a vibration element can be included.

28 Claims, 9 Drawing Sheets

(58) Field of Classification Search
CPC .... A61H 2009/0064; A61H 2201/5097; A61H 2201/0157; A61H 2201/503; A61H 2201/501; A61H 9/0057
See application file for complete search history.

(56) References Cited

U.S. PATENT DOCUMENTS

| | | | | |
|---|---|---|---|---|
| 4,196,722 | A * | 4/1980 | Vanderwoude | A61H 31/007 601/41 |
| 4,429,688 | A * | 2/1984 | Duffy | A61H 31/00 601/41 |
| 5,039,045 | A * | 8/1991 | Adams | A45D 42/14 248/309.3 |
| 5,645,522 | A * | 7/1997 | Lurie | A61H 31/007 607/142 |
| 5,902,293 | A * | 5/1999 | Liu | A61H 9/005 604/74 |
| 6,143,391 | A | 11/2000 | Barnes et al. | |
| 6,517,499 | B1 | 2/2003 | Pereira | |
| 6,733,438 | B1 | 5/2004 | Dann et al. | |
| 6,949,067 | B1 | 9/2005 | Dann et al. | |
| 7,850,891 | B2 | 12/2010 | Iida et al. | |
| 8,251,323 | B2 * | 8/2012 | Liu | F16B 47/00 248/205.5 |
| 10,577,521 | B2 | 3/2020 | Myers | |
| 2002/0002346 | A1 * | 1/2002 | Horst | A61H 9/005 601/6 |
| 2003/0109815 | A1 | 6/2003 | Horst | |
| 2006/0206000 | A1 | 9/2006 | Gloth | |
| 2006/0235339 | A1 | 10/2006 | Naldoni | |
| 2008/0086065 | A1 * | 4/2008 | Holm | A61H 23/008 601/107 |
| 2008/0106896 | A1 | 5/2008 | Liu et al. | |
| 2011/0295162 | A1 * | 12/2011 | Chang | A61H 9/0057 601/6 |
| 2013/0072866 | A1 | 3/2013 | Hegen | |
| 2013/0123674 | A1 | 5/2013 | Carter et al. | |
| 2015/0283022 | A1 | 10/2015 | Lee et al. | |
| 2015/0313788 | A1 | 11/2015 | Conte et al. | |
| 2016/0000644 | A1 | 1/2016 | Makower et al. | |
| 2017/0290732 | A1 | 10/2017 | Palomaki et al. | |
| 2018/0325768 | A1 | 11/2018 | Cote | |
| 2018/0339090 | A1 * | 11/2018 | Santana | A61M 1/08 |
| 2019/0275771 | A1 | 9/2019 | Myers | |
| 2020/0390948 | A1 * | 12/2020 | Liu | A61H 9/0057 |
| 2022/0387678 | A1 * | 12/2022 | Park | A61M 1/80 |
| 2022/0395421 | A1 | 12/2022 | Brown | |
| 2023/0263697 | A1 | 8/2023 | Liu et al. | |

FOREIGN PATENT DOCUMENTS

| | | | | |
|---|---|---|---|---|
| CN | 107865987 | A | 4/2018 | |
| CN | 208081584 | U | 11/2018 | |
| DE | 202013003613 | U1 | 6/2013 | |
| EP | 2853250 | A1 * | 4/2015 | A61H 7/008 |
| JP | 3045746 | | 2/1998 | |
| JP | 2001120615 | A * | 5/2001 | |
| KR | 2001169844 | Y1 | 2/2000 | |
| KR | 10-1626203 | B1 | 5/2016 | |
| KR | 101620010 | B1 * | 5/2016 | A61H 9/00 |
| WO | 2022/035753 | A1 | 2/2022 | |

OTHER PUBLICATIONS

International Search Report and Written Opinion in counterpart International Application No. PCT/US21/45207 dated Nov. 30, 2021, pp. 1-26.

International Preliminary Report on Patentability in counterpart International Application No. PCT/US21/45207 dated Dec. 23, 2022, pp. 1-6.

First Examination Report in counterpart Indian Patent Application No. 2023-37005545 dated Jan. 6, 2026, pp. 1-8.

Translation of JP 2001/120615. Accessed from PE2E-SEARCH on Jun. 26, 2026. (Year: 2001). pp. 1-6.

Translation of KR 101620010. Accessed from PE2E-SEARCH on Jun. 26, 2026. (Year: 2016). pp. 1-6.

Translation of KR 2001/69844. Accessed from PE2E-SEARCH on Jun. 26, 2026. (Year: 2000). pp. 1-6.

* cited by examiner

CUPPING DEVICE, SYSTEM, AND FEATURES

CROSS-REFERENCE TO PRIORITY APPLICATION

This application claims the benefit of U.S. Provisional Patent Application No. 63/063,537 filed Aug. 10, 2020, and entitled Improved Cupping Therapy, which is incorporated herein by reference in its entirety.

BACKGROUND

The present invention generally relates to therapy and/or massage equipment and, more particularly, to cupping therapy.

It is known to use a transparent, elastomeric silicone cup for cupping therapy. The cup can be manually partially collapsed, and then the cup can be allowed to elastically expand while the cup's opening is engaged against a user's skin, so that the resulting partial vacuum in the cup causes the cup's opening to be attached to the skin, and suctional force is applied to the skin. The suction on the skin can provide a therapeutic effect.

It is known for suction cups that may be used for cupping therapy to be made of a single homogeneous material, with different cups having different durometers. This can pose difficulties as the stiffer cups may not maintain suction around smaller, narrow, or more rounded body parts, for example forearms. Alternatively, the known softer cups offer more adhesion to the skin but can collapse on themselves rendering them difficult to use as a massage tool.

There is a desire for improvements associated with cupping therapy (e.g., improved ease of use, and improved therapeutic effects).

SUMMARY

An aspect of this disclosure is the provision of an improved suction cup configured for use in cupping therapy (e.g., massage). The suction cup includes a body including at least one sidewall extending at least partially around an interior space and at least one rim extending around an opening to the interior space. At least a portion of the body can be elastic and configured so that the body is both (i) capable of being squeezed to transition the body from an at-rest configuration to a partially-collapsed configuration, and (i) elastically biased toward the at-rest configuration. The volume of the interior space of the body is greater in the at-rest configuration than in the partially-collapsed configuration. The rim and/or a closed end of the body can be less stiff than a portion of the sidewall that is spaced apart from the rim. A vibrator, strap, over-molded part, under-molded part, and/or other suitable features can be associated with (e.g., mounted to, embedded in, and/or otherwise associated with) the body of the suction cup.

An example of this disclosure is the provision of a suction cup that has a relatively soft lip/open end for optimal adhesion to the user's body with a fortification of the body of the cup to better maintain its shape for enhanced ease of use, and a vibration element may be included for optimal results.

The foregoing summary provides a few brief examples and is not exhaustive, and the present invention is not limited to the foregoing examples. The foregoing examples, as well as other examples, are further explained in the following detailed description with reference to accompanying drawings.

BRIEF DESCRIPTION OF THE DRAWINGS

The drawings are provided as examples, and they are schematic and may not be drawn to scale. The present invention may be embodied in many different forms and should not be construed as limited to the examples depicted in the drawings.

FIG. 2 is an isolated, front elevation view of the suction cup of FIG. 1 in its at-rest configuration, wherein FIG. 2 is also representative of right, left, and rear elevation views of the suction cup of FIG. 1.

DETAILED DESCRIPTION

Examples of embodiments are disclosed in the following. The present invention may, however, be embodied in many different forms and should not be construed as limited to the embodiments set forth herein. For example, features disclosed as part of one embodiment or example can be used in the context of another embodiment or example to yield a further embodiment or example. As another example of the breadth of this disclosure, it is within the scope of this disclosure for one or more of the terms "substantially," "about," "approximately," and/or the like, to qualify each of the adjectives and adverbs of the Detailed Description section of disclosure, as discussed in greater detail below.

Figure 1:
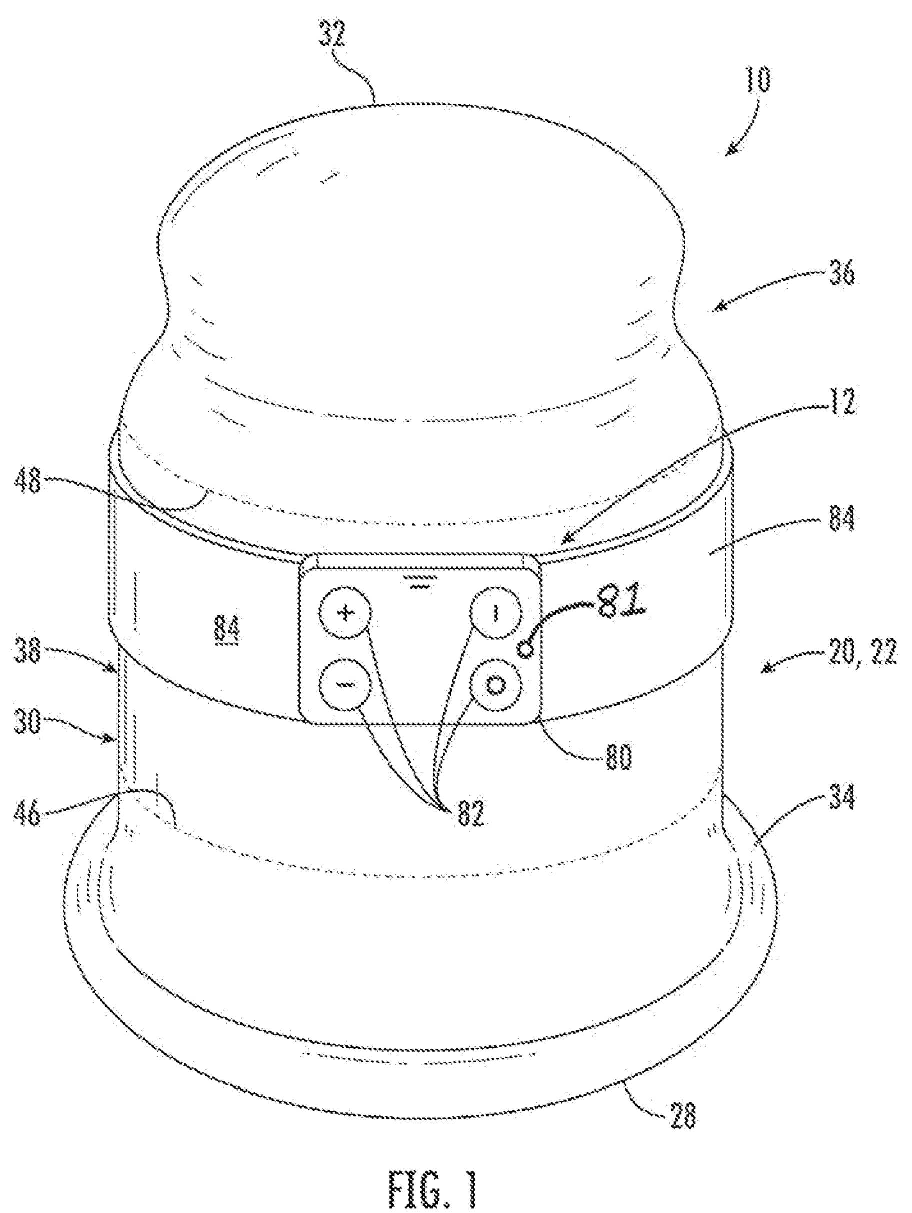
FIG. 1 is a top, front pictorial view of a therapeutic system including a vibration apparatus mounted to a suction cup, wherein the suction cup is depicted in its at-rest configuration, in accordance with a first embodiment of this disclosure.

FIG. 1 schematically depicts a therapeutic system 10 that includes a vibration apparatus 12 mounted to a suction cup 20, in accordance with a first embodiment of this disclosure. The first embodiment suction cup 20 is configured (e.g., is at least partially collapsible and elastomeric) so that it can be used for cupping therapy (e.g., massage). More specifically, the suction cup 20 can be manually operated to create a partial vacuum that is used to removably mount the suction cup on the skin of a user, and apply a suctional force to the skin (not depicted in the drawings).

The optional vibration apparatus 12 can be operated during the cupping therapy in a manner that vibrates each of the suction cup 20, the associated skin, and underlying tissue (e.g., tendon(s)) in a manner that enhances the therapeutic effects of the cupping therapy. It is believed that the added vibrations aid in blood flow and aid in breaking up tissue adhesions. The vibration apparatus 12 may be a permanent part of the suction cup 20, or it may optionally be added to the suction cup as an accessory. For example, the vibration apparatus 12 can be removably mounted to the suction cup 20, as discussed further below. As an example, the vibration apparatus 20 may be characterized as being a part of the suction cup 20.

Figure 4:
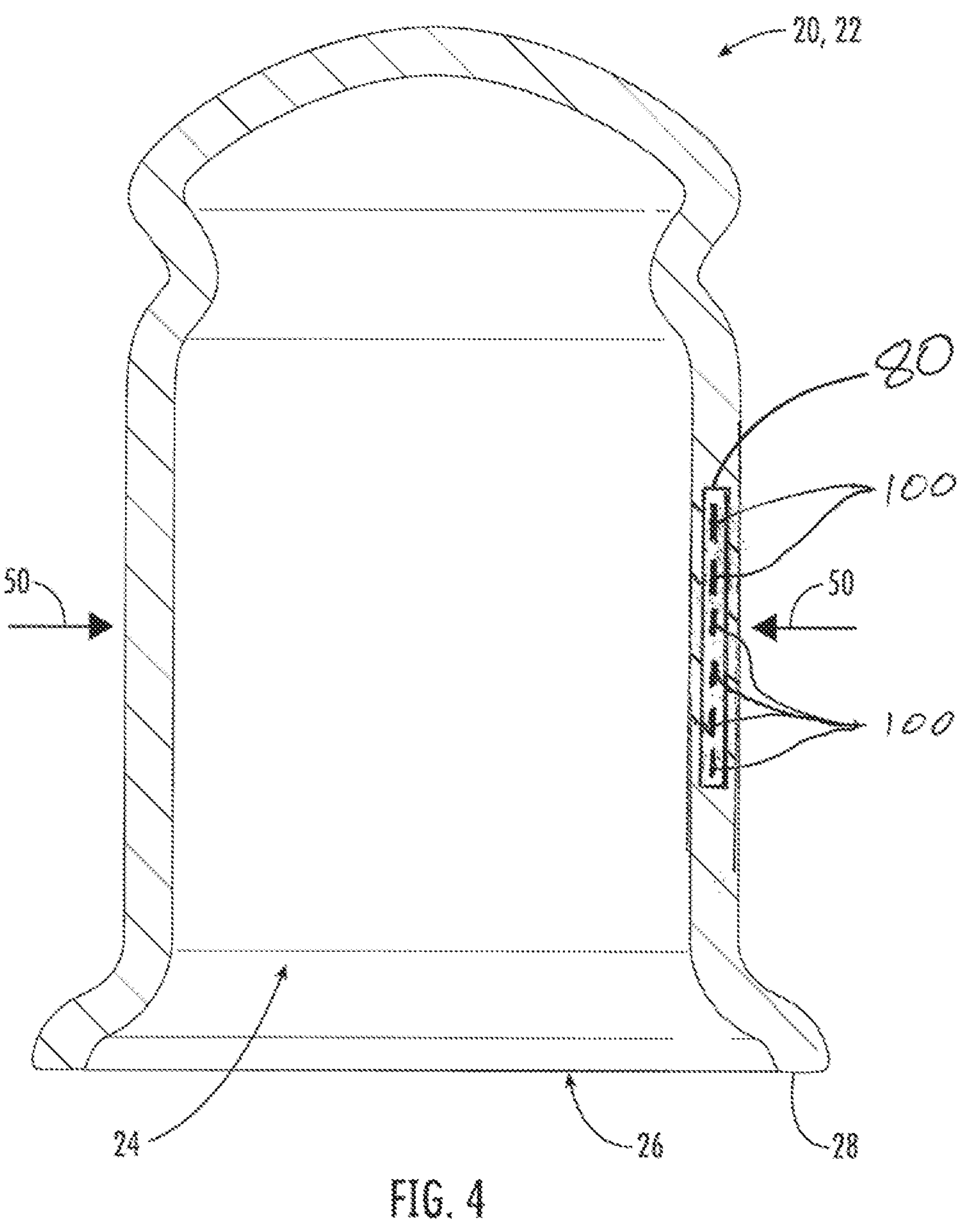
FIG. 4 is a cross-sectional view taken along line 4-4 of FIG. 3 (i.e., the cutting plane defining FIG. 4 intersects the entire length of the lengthwise axis of the suction cup), wherein FIG. 4 further schematically depicts that a housing and/or any other stiffening features may be embedded in the body of the suction cup.

Referring also to FIG. 4, the suction cup 20 can comprise, consist essentially of, or consist of a deformable, container-shaped body 22 that defines an interior space 24 (FIG. 4) of the suction cup. In the first embodiment, the interior space 24 is only open at a single opening 26 (FIG. 4) defined by at least one rim 28 (e.g., an annular rim) of the body. The rim 28 is configured to be engaged against the user's skin, so that the user's skin closes the opening 26. FIG. 4 can be further described as schematically depicting that the body 22, or more specifically the at least one sidewall 30 of the body, can include one or more embedded stiffening elements or features, as may be generally understood with reference to the feature identified by reference numeral 80 in FIG. 4, and as discussed further below.

The first embodiment body 22 comprises, consists essentially of, or consists of elastomeric material so that the cup 20 can be manually squeezed to transition the body from an at-rest configuration (FIGS. 1-4) to an initial partially-collapsed configuration (not depicted in the drawings). The cup 20 is configured so that, allowing the body 22 to transition from the initial partially-collapsed configuration toward the at-rest configuration (e.g., by ceasing the manual squeezing, and in response to the body being elastically biased toward the at-rest configuration), while the rim 28 is engaged against skin that closes the opening 26, a partial vacuum is created in the interior space 24. As a result, suctional force is applied to the skin, and the opening 26 and/or rim 28 are attached to the skin (e.g., the suction cup 20 is removably mounted to the skin).

Depending upon the configuration and properties of the suction cup 20 and the tissue to which the cup is mounted, the cup may not reach the at-rest configuration when the cup is mounted to the skin as discussed above. That is, the combination of the cup 20 mounted to the skin may reach an equilibriums configuration in which the cup is in an intermediate partially-collapsed configuration that is between its at-rest configuration and the initial partially-collapsed configuration. That is, the degree to which the cup 20 is collapsed is greater in the initial partially-collapsed configuration than in the intermediate partially-collapsed configuration. The volume of the interior space 24 is greater in the at-rest configuration than in both of the initial and intermediate partially-collapsed configurations. The volume of the interior space 24 is greater in the intermediate partially-collapsed configuration than in the initial partially-collapsed configuration.

Figure 2:
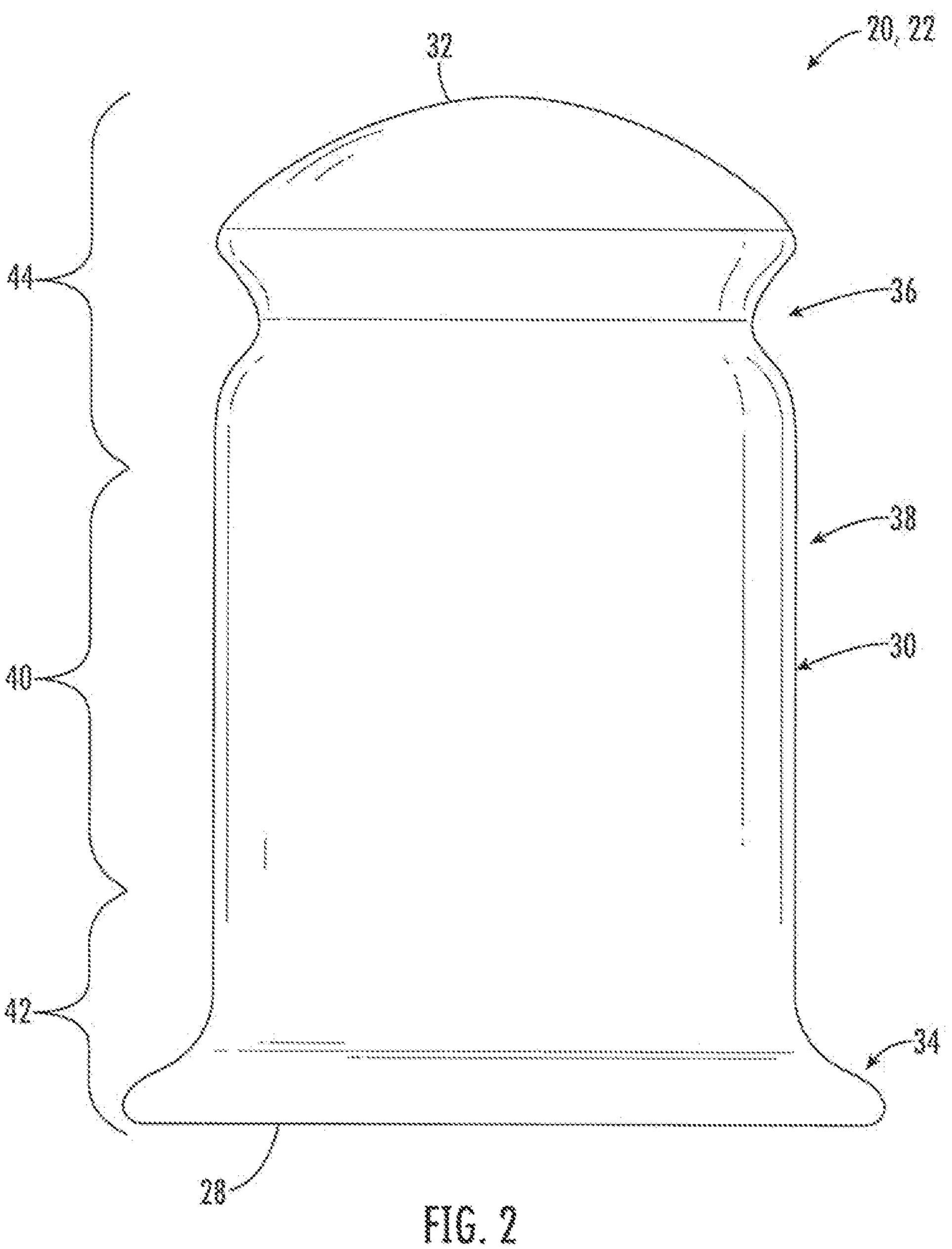
Figure 3:
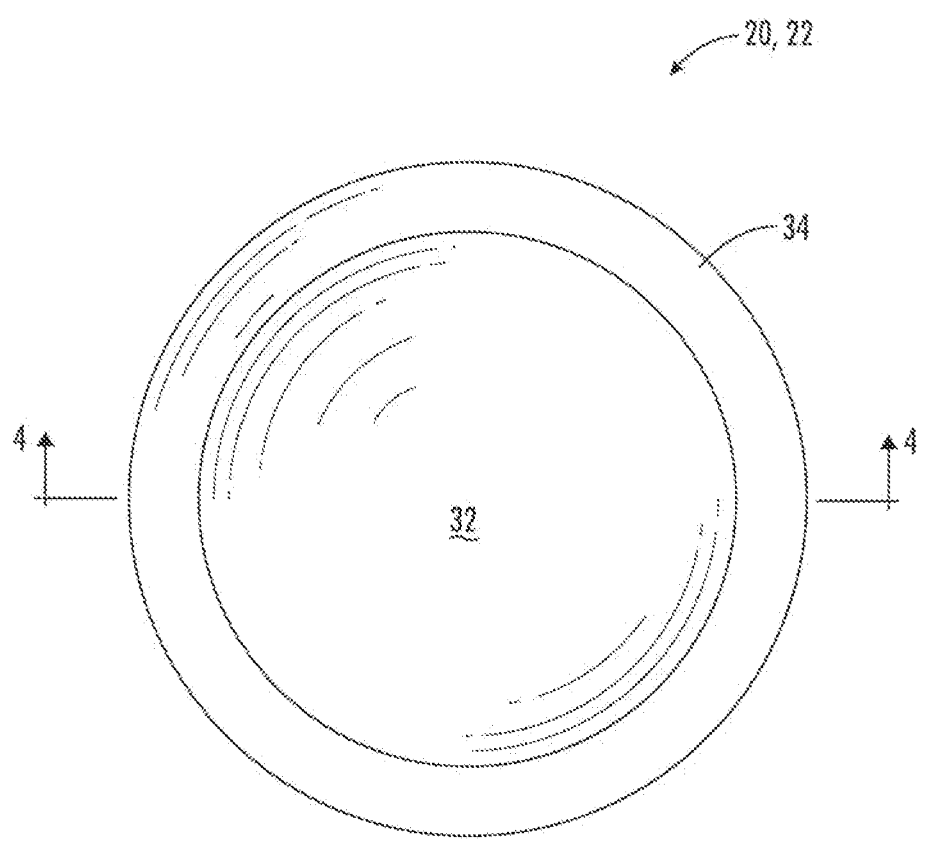
FIG. 3 is an isolated, top plan view of the suction cup of FIG. 1 in its at-rest configuration.

In the orientation of the first embodiment cup 20 depicted in FIGS. 1 and 2, the rim 28 is a lower annular edge of at least one sidewall 30 (e.g., an upright annular sidewall), the sidewall extends upwardly to a domed upper wall 32, and the upper wall fully and permanently closes the upper end of the cup. A lower portion of the at-rest sidewall 30 can be in the form of smoothly shaped, outwardly extending, annular flange 34 portion that includes the rim 28. An upper portion of the at-rest sidewall 30 can be in the form of smoothly shaped, annular undulated wall portion 36 (e.g., an annular pleat-like or bellows-like portion). An intermediate portion of the at-rest sidewall 30 can be in the form of a cylindrical wall portion 38 that connects the flange 34 to the undulated wall portion 36 (e.g., an annular groove). As depicted in FIGS. 1 and 2, an upper annular portion of the undulated wall portion 36 can be connected to an outer annular portion of the upper wall 32.

Referring to FIG. 2, the first embodiment cup body 22 includes an intermediate portion 40 between opposite open and closed end-portions 42, 44 of the cup body. In FIG. 1, the boundary 46 between the body's intermediate portion 40 and the body's lower, open end-portion 42 is schematically depicted by a lower dashed boundary line 46; and the boundary 48 between the intermediate portion 40 and the upper, closed end-portion 44 is schematically depicted by an upper dashed boundary line 48. In accordance with an example of a method of using the cup 20 for cupping therapy, the step of partially collapsing the body 22 comprises a user manually squeezing the intermediate portion 40 with one of their hands, between their thumb and fingers, to provide opposite compressive forces schematically depicted in FIG. 4 by arrows 50.

In the first embodiment, one or more of, or each of, the intermediate portion 40, the open end-portion 42, and the closed end-portion 44 comprises, consists essentially of, or consists of elastomeric material such as silicone; the intermediate portion 40 (e.g., its elastomeric material) is harder and/or stiffer than (e.g., has a higher modulus of elasticity than) the open end-portion 42 (e.g., its elastomeric material); the intermediate portion 40 (e.g., its elastomeric material) is harder and/or stiffer than (e.g., has a higher modulus of elasticity than) the closed end-portion 44 (e.g., its elastomeric material); and the open and closed end-portions 42, 44 (e.g., their elastomeric materials) have about the same hardness and stiffness (e.g., about the same modulus of elasticity). In an alternative embodiment, the intermediate portion 40 and closed end-portion 44 may be formed of the same elastomeric material and have the same hardness, stiffness, and/or modulus of elasticity, such that there may not be a boundary (see, e.g., boundary 48) between the intermediate and closed end-portions 40, 44.

In the first embodiment, the relatively hard and/or relatively stiff material that defines or partially defines the body's intermediate portion 40 can be partially collapsed and then be released to provide a relatively high vacuum that can be maintained during cupping therapy. During cupping therapy in accordance with a method of the first embodiment, the relatively soft and/or relatively flexible material that defines or partially defines the body's closed end-portion 44 allows the closed end-portion to be easily manually manipulated to adjust the vacuum/suction. For example, for adjusting the vacuum/suction during cupping therapy, the domed upper wall 32 can be manually depressed, so that the apex of the domed upper wall moves inwardly relative to the interior space 24 (FIG. 4).

During cupping therapy in accordance with a method of the first embodiment, the relatively soft and/or relatively flexible material that defines or partially defines the open end-portion 42 allows a user to relatively easily glide the rim 28 across their skin and/or around curved portions of their body without losing suction. For example, the rim 28 can be guided around curves of the user's arms for treating tendonitis. For promoting easy gliding, bath water, shower water, and or lubricants (e.g., oils) may be present on the skin. Accordingly, the system 10, or respective components thereof, may be waterproof, readily cleanable, and/or the like. Differently sized cup bodies 22 can be used for treating different body parts.

Figure 5:
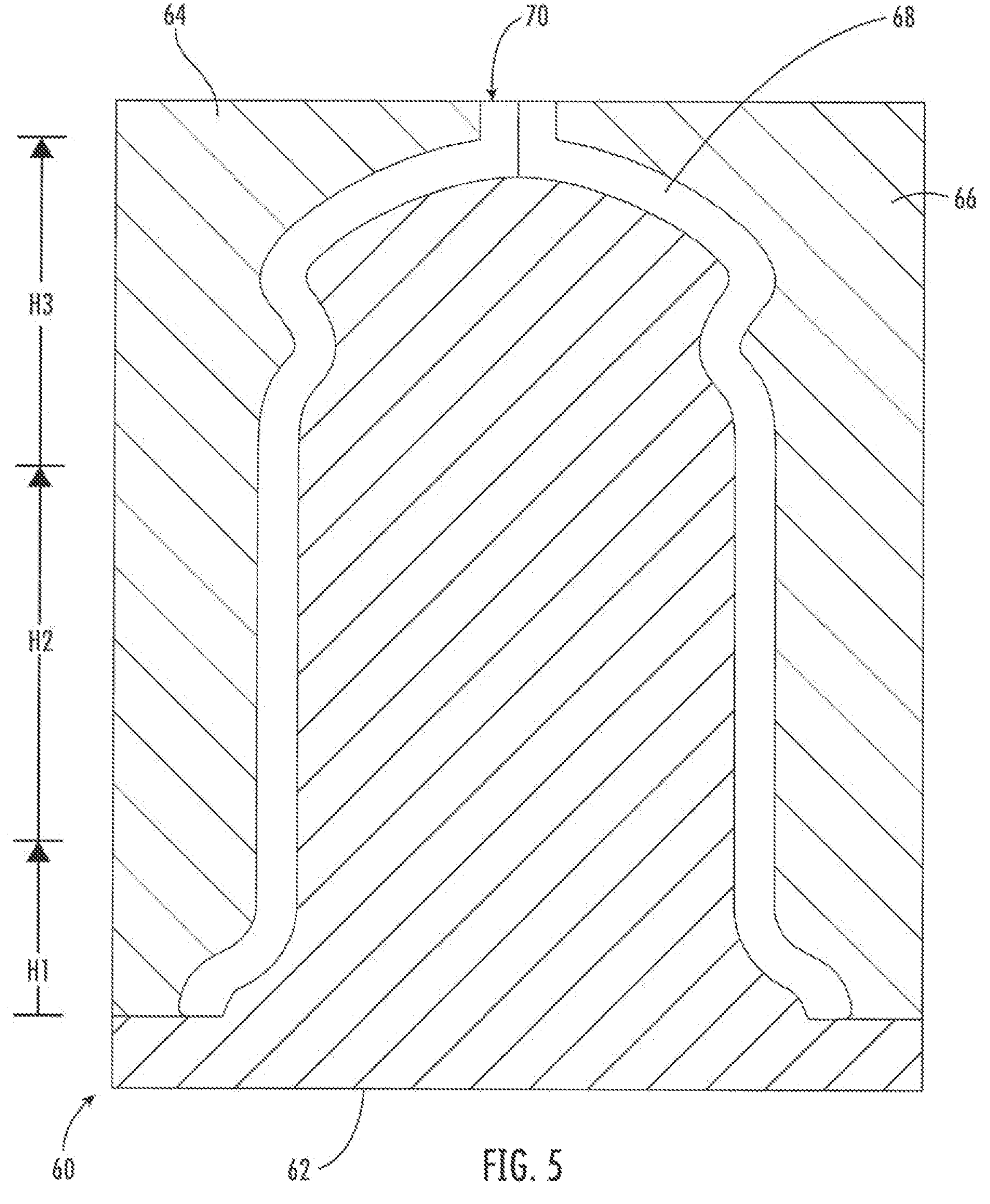
FIG. 5 is a cross-sectional view of at least a portion of a mold assembly that may be used in the manufacture of the suction cup, wherein the mold is in its closed configuration, and the cutting plane defining FIG. 5 intersects the entire length of the lengthwise axis of the closed mold, in accordance with the first embodiment.

Referring to FIG. 5, it is believed that the first embodiment cup body 22 can be formed (e.g., by way of transfer molding or another suitable molding process) in a mold assembly 60 including at least an inner mold member 62 and opposite outer mold members 64, 66, or the like, at least some of which are movable relative to one another between open and closed configurations. In the closed configuration of the mold 60, a cavity 68 corresponding in shape to the at-rest shape of the cup body 22 is defined between the mold members 62, 64, 66, and the cavity is closed except for being open at one or more access or injection ports 70.

Referring to FIGS. 2 and 5, in accordance with an example of a method of the first embodiment, it is believed that liquid molding material for forming the open end-portion 42 can be introduced into the cavity 68 through the port 70 and/or other suitable port(s) until that liquid molding material reaches a height of H1, then liquid molding material for forming the intermediate portion 40 can be introduced into the cavity 68 through the port 70 and/or other suitable port(s) until that liquid molding material reaches a height of H2, and then liquid molding material for forming the closed end-portion 44 can be introduced into the cavity 68 through the port 70 and/or other suitable port(s) until that liquid molding material reaches a height of H3. In accordance with a method of the first embodiment, it is believed that the liquid molding materials can remain stratified (e.g., substantially, generally, or somewhat stratified) along the boundary lines 46, 48 (FIG. 1), and that cross-linking (curing) can occur in the molding materials of the intermediate portion 40, the closed end-portion 44, and the open end-portion 42 and across the boundary lines 46, 48 so that the opposite lower and upper ends of the intermediate portion 40 are fixedly connected to the open and closed end-portions 42, 44, respectively, and the cup body 22 is a unitary article of manufacture that normally does not include separable parts.

It is believed that the liquid molding material of the open end-portion 42, the intermediate portion 40, and the closed end-portion 44 can be concurrently (e.g., simultaneously) and/or sequentially cross-linked (cured), for example, concurrently and/or sequentially heated to a temperature sufficient to initiate cross-linking (curing). For example, it is believed that the liquid molding material for forming the open end-portion 42, the intermediate portion 40, and the closed end-portion 44 can be introduced into the cavity 68 sequentially as discussed herein and then all together be simultaneously subjected to cross-linking (curing) conditions to form the unitary product. Alternatively, it is believed the liquid molding material for forming the open end-portion 42 can be introduced into the cavity 68 and then be at least partially cross-linked (cured); thereafter the liquid molding material for forming the intermediate portion 40 can be introduced into the cavity 68 and then be at least partially cross-linked (cured) to fixedly connect the lower end of the intermediate portion 40 to the open end-portion 42; and thereafter the liquid molding material for forming the closed-end portion 44 can be introduced into the cavity 68 and then be at least partially cross-linked (cured) to fixedly connect the upper end of the intermediate portion 40 to the closed end-portion 44. Cross-linking (curing) the molding material of the lower end-portion 42, the intermediate portion 40, and/or the closed end-portion 44 can be completed during and/or after any of the sequential cross-linking (curing) steps.

In accordance with a primary example of the first embodiment (i.e., for example, and not for the purpose of limiting the scope of this disclosure), the cup body 22 can comprise, consist essentially of, or consist of transparent silicone (e.g., crosslinked silicone) that may optionally be colored. In this regard, it is believed that the above-discussed liquid molding materials may each comprise liquid silicone, one or more crosslinking (curing) agents, and one or more other materials (e.g., fillers and/or additives (e.g., colorants)), wherein the amounts and/or types of additives and/or fillers may respectively vary between the portions 40, 42, 44 (FIG. 2) in a manner that causes the properties of the portions 40, 42, 44 to vary in the manner discussed above. Alternatively, the cup body 22 may not be transparent and/or the cup body may be made of other suitable materials, for example polymeric materials that are elastomeric (e.g., rubber).

The cup 20 can include visual indicators or indications for aiding a user of the cup 20. For example, one or more of the boundaries 46, 48 (FIG. 1) may be identified by an actual annular line and/or by adding differently colored colorants (e.g., pigments) to the liquid molding materials respectively for the portions 40, 42, 44 (FIG. 2). The cup 20 can include any suitable colors or color combinations. For example, two or more different cup portions (e.g., portions 40, 42, and/or 44) can be colored differently from one another in a manner that seeks to identify (e.g., by color contrast(s)) to a user the variations in the hardness and/or stiffness of the cup portions. As another example of possible visual indicators or indications for aiding a user of the cup 20, graphics (e.g., images, text, shapes, indicia, patterns, solid areas, or any other printing) may be included on the cup 20. Such visual indicators or indications can seek to help to inform the user how or where to manually manipulate the cup 20 and/or inform the user where to mount the vibration apparatus 12 (FIG. 1) on the cup.

Referring to FIG. 1, the schematically depicted vibration apparatus 12 can include a housing 80 containing, for example, internal features including a battery that powers an electric motor having a rotary output shaft to which an eccentric mass is connected, and a controller (e.g., computer processer, programmable logic device (PLD), and/or application specific integrated circuit (ASIC), as discussed further below. In one example, the one or more batteries of the vibration apparatus 20, or more specifically the battery(s) carried by or associated with the housing 80, can be configured to be recharged by way of a charging port 81 that receives the free end of a charging cable extending from an external electric power source. Alternatively, the batteries can be recharged by a charging pad, or the like, or in any other suitable manner, as discussed further below. As another example, the batteries may be replaceable.

The vibration apparatus 12 can include a user interface for allowing a user to control operation of the vibration apparatus. For example, FIG. 1 schematically depicts that such a user interface can include one or more manually-actuatable push-buttons 82 accessible at an outer face of the housing 80. The buttons 82 and/or other suitable features can be operatively associated with the controller for respectively turning the vibration apparatus 12 off and on (e.g., the vibration apparatus vibrates when "on" and does not vibrate when "off"), and increasing or decreasing the strength or energy (e.g., frequency and/or magnitude) of the vibrating. Further, the vibration apparatus 12 can be configured to provide a variety of different vibration waveforms. A variety of differently configured (e.g., differently operable) vibration apparatus 12 are within the scope of this disclosure. For example, the one or more buttons 82 can be arranged in any suitable configuration (e.g., side-by-side in a single row). As further examples, the user interface of the vibration apparatus 12 can include or consist of a manually operatable rocker switch; a touchscreen; a single button that could be operated to power on, cycle through several massage options, and power off; and/or other suitable features. Other features that may be associated with the vibration apparatus 12 are discussed below.

With continued reference to FIG. 1, the vibration apparatus 12 can further include at least one strap 84 (e.g., band) to which the housing 80 is securely (e.g., fixedly, yet removably) mounted, and the housing can be securely (e.g., fixedly, yet removably) mounted to the cup body 22 by way of the strap. The strap 84 can be a one-piece or two-piece strap connected to the housing 80 in any suitable manner (e.g., by way of one or more bars or slots, fixed bars, spring bars, or the like, that are not depicted in the drawings). For attaching and removing the vibration apparatus 12 from the cup body 22, and adjusting the length of the strap 84 for use with differently sized cup bodies, the strap typically includes and/or is associated with one or more conventional buckles, clasps, and/or length adjustment features that are hidden from view on the far side of the system 10 in FIG. 1.

The vibration apparatus 12, if present, can be mounted at any suitable location along the length of the cup 12, and it may typically be mounted at any suitable location along the length of the relatively rigid portion (e.g., the intermediate portion 40) of the cup 12. For example and in contrast to the configuration depicted in FIG. 1, the vibration apparatus 12 can be more proximate or adjacent the boundary 46 between the intermediate and open end portions 40, 42 (FIG. 2). Alternatively, the vibration housing 80 can be associated with (e.g., mounted to, embedded in, and/or otherwise associated with) the cup body 22 in any other suitable manner, as discussed further below.

Referring again to FIG. 1, in an alternative embodiment, the suction cup 20 can be formed of a single and/or uniform type of elastomeric material (e.g., each of the intermediate portion 40, the open end-portion 42, and the closed end-portion 44 comprises, consists essentially of, or consists of a single and/or uniform type of elastomeric material such as silicone). In this embodiment, the intermediate portion 40, the open end-portion 42, and the closed end-portion 44 (e.g., their elastomeric materials) can have about the same hardness and/or stiffness (e.g., about the same modulus of elasticity). To provide a zone (e.g., portion) of the body 22 having a different hardness and/or stiffness as compared to other zones (e.g., other portions) of the body 22, the therapeutic system 10 can further include at least one strap (e.g., band) such as strap 84 (with or without housing 80 as described herein) cooperatively configured with (e.g., mounted to) the intermediate portion 40 of the body 22. The strap 84 can be formed of a material that is harder and/or stiffer than (e.g., has a higher modulus of elasticity than) the elastomeric material of the open end-portion 42, the intermediate portion 40, and the closed end-portion 44. The relatively increased hardness and/or stiffness of the strap 84 can provide a zone of increased stiffness to the body 22. Alternatively, or in addition, the increased hardness and/or stiffness can be attributed to the increased thickness of the portion of the suction cup including both the intermediate portion 40 and the strap 84. As other examples, the strap 84 can be formed of a material that is less hard and/or less stiff (e.g., has a lower modulus of elasticity) as compared to the material of the open end-portion 42, the intermediate portion 40, and/or the closed end-portion 44.

The strap can be detachable (removable). Again, for attaching and removing the strap 84, and adjusting the length of the strap 84 for use with differently sized cup bodies, the strap typically includes and/or is associated with one or more conventional buckles, clasps, and/or length adjustment features that are hidden from view on the far side of the system 10 in FIG. 1.

Numerous variations are within the scope of this disclosure. For example, the cup sidewall 30 may include a greater or lesser number of wall portions (e.g., wall portions 34, 36, 38 of FIG. 1) and/or the cup body 22 may include a greater or lesser number of body portions (e.g., body portions 40, 42, 44 of FIG. 2). For example, the cup 20 may include one or more additional annular grooves and/or undulated wall portions (see, e.g., annular groove and/or undulated wall portion 36), and the vibration apparatus' strap 84 (FIG. 1) may be nested into such an annular groove that functions as a receptacle for at least partially receiving the strap. Additionally or alternatively, the cup 20 can include one or more other features for facilitating mounting or positioning of the vibration apparatus 12, for example notches, catches, latches, and/or graphics (e.g., images, text, shapes, indicia, patterns, solid areas, or any other printing).

In accordance with an example described above, it is believed that the cup body 22 can be a unitary article of manufacture formed within a single mold 60 assembly (e.g., by way of multi-shot or sequential injection molding). Alternatively, it is believed that one or more portions of the cup body 22 (e.g., one or more of the portions 40, 42, 44 of FIG. 2) can be originally formed separately from one another in any suitable manner (e.g., injection molding, extruding, compression molding, and/or transfer molding) and thereafter be joined together in any suitable manner with connector(s), adhesive(s) (e.g., silicone adhesive), and/or by way of suitable molding techniques (e.g., insert molding, over molding, or the like) to form the cup body. Reiterating, the cup body 22 of the first embodiment can be at least partially formed by way of over molding, as discussed further below with reference to FIGS. 7 and 8.

In some embodiments, one or more portions of the cup body 22 (e.g., one or more of the portions 40, 42, 44 of FIG. 2) can be mechanically joined together (e.g., mechanically connected, attached, fastened, etc.) to form the cup body 22. For example, one or more portions of the cup body 22 (e.g., one or more of the portions 40, 42, 44 of FIG. 2) can be mechanically joined (mechanically connected, mechanically attached, mechanically fastened, etc.) using mechanical fasteners (mechanical connectors, mechanical joints, etc.), that are separate from (not integrated with) the one or more portions to form the cup body 22. Exemplary mechanical fasteners (mechanical connectors, etc.) that are separate from the portions can include but are not limited to screws, rivets, pins, anchors, and the like.

As another example, one or more portions of the cup body 22 (e.g., one or more of the portions 40, 42, 44 of FIG. 2) can be mechanically joined (e.g., mechanically connected, mechanically attached, mechanically fastened, etc.) using integrated interlocking fasteners (e.g., integrated interlocking connectors, etc.), formed as integral parts of one or more of the portions of the cup body 22 during molding. In some embodiments, the intermediate portion can have an upper end and a lower end opposite one another, with the upper end in a facing relationship with the closed end-portion and the lower end in a facing relationship with the open end-portion. The upper end of the intermediate portion and the closed end-portion each can include integrated connectors that interlock with one another to attach the intermediate portion and the closed end-portion. In addition, or in the alternative, the lower end of the intermediate portion and the open end-portion each can include integrated connectors that interlock with one another to attach the intermediate portion and the open end-portion.

Integrated mechanical fastening systems can include without limitation snap-fit connectors, tongue-and-groove connectors, and the like. For example, one or more portions of the cup body 22 (e.g., one or more of the portions 40, 42, 44 of FIG. 2) can be mechanically joined using a snap-fit connection, in which one or more portions of the cup body 22 include an integrated molded protrusion configured (shaped) to insert into a corresponding integrated molded "snap-in" area (e.g., recess, cut-out, slot, etc.) of one or more of other portions to form a mechanical joint system when the protrusion is inserted into/interlocked with the snap-in area. As another example, one or more portions of the cup body 22 (e.g., one or more of the portions 40, 42, 44 of FIG. 2) can be mechanically joined using a tongue-and-groove connection, in which one or more portions of the cup body 22 can include an integrated molded slot (groove) along an edge configured (shaped) to tightly and fixedly receive a corresponding integrated molded ridge (tongue) along an edge of one or more other portions to form a mechanical joint system when the tongue is tightly and fixedly inserted into the groove.

In some embodiments, one or more portions of the cup body 22 (e.g., one or more of the portions 40, 42, 44 of FIG. 2) can be adhesively joined (e.g., adhesively connected, attached, fastened, etc.) using adhesives known in the art for adhering elastomeric (e.g., silicone) materials. In some embodiments, the intermediate portion 40 can have an upper end and a lower end opposite one another, with the upper end in a facing relationship with the closed end-portion 44 and the lower end in a facing relationship with the open end-portion 42. The cup body 22 can include an adhesive layer disposed on the upper end of the intermediate portion such that the adhesive layer is positioned between the intermediate layer and the closed end-portion and adheres the intermediate layer and the closed end-portion. In addition, or in the alternative, the cup body can include an adhesive layer on the lower end of the intermediate portion such that the adhesive layer is positioned between the intermediate layer and the open end-portion and adheres the intermediate layer and the open end-portion.

Examples of adhesives include without limitation silicone-based adhesives, such as silicone-epoxy-based adhesives, and/or cyanoacrylate-based adhesives. Reference is made, for example, to US 2019/0275771 to Meyers, published Sep. 12, 2019, now U.S. Pat. No. 10,577,521 issued Mar. 3, 2020, the entire disclosure of each of which is incorporated herein by reference.

Figure 6:
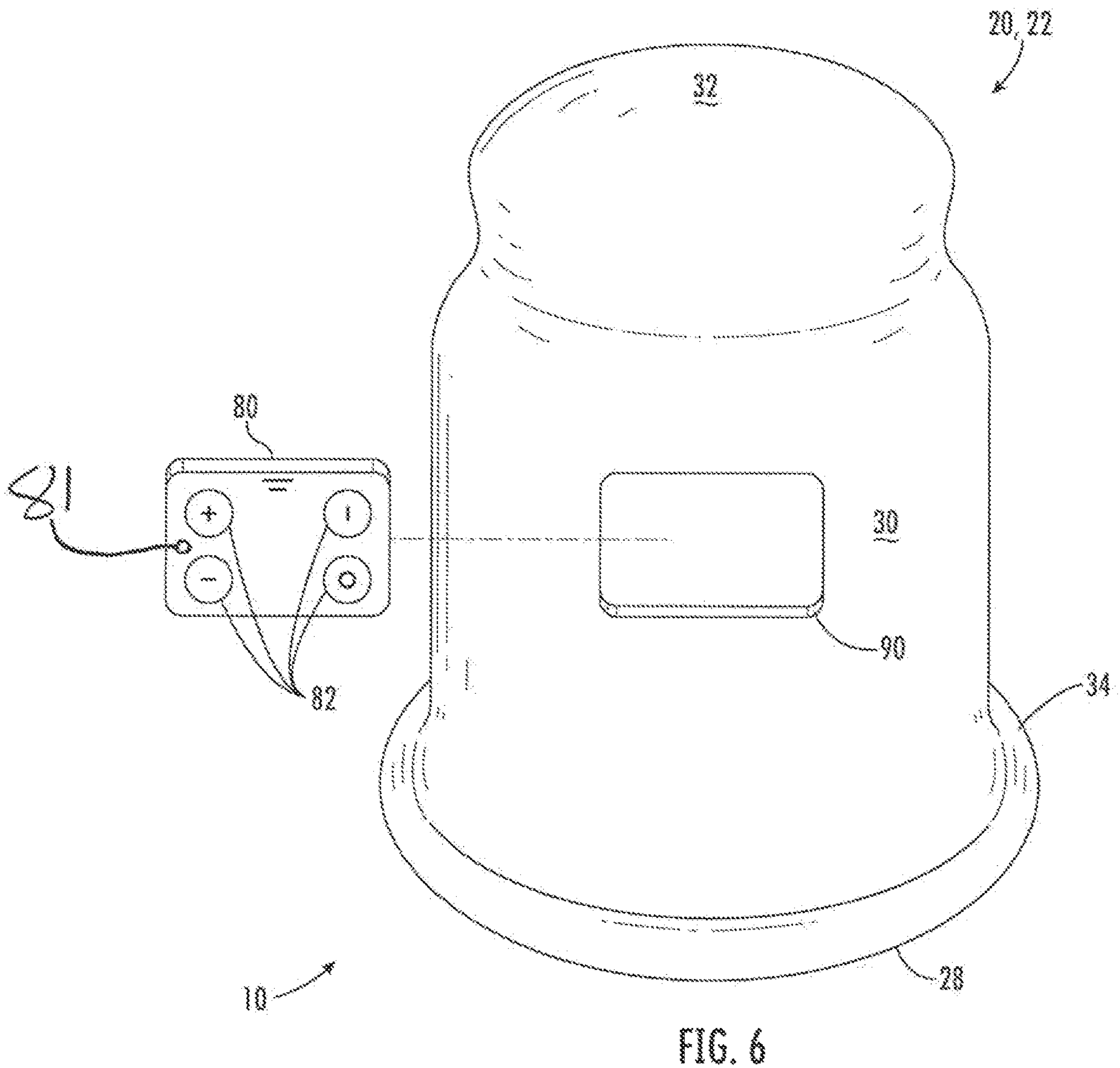
FIG. 6 is an exploded, front pictorial view of a therapeutic system in accordance with a second embodiment of this disclosure.

Other variations are also within the scope of this disclosure. For example, FIG. 6 depicts a system 10 in accordance with a second embodiment of this disclosure. The first and second embodiments can be alike, except for variations noted and variations that will be apparent to those of ordinary skill in the art.

In the second embodiment, the at least one sidewall 30 defines a cavity or receptacle for removably receiving the vibration apparatus' housing 80 by way of an interference fit and/or in any other suitable manner, typically so that the housing can be securely (e.g., fixedly yet removably) mounted to the cup body 22. Alternatively, the vibration apparatus' housing 80 may be mounted to, or operatively associated with, the cup body 22 in any other suitable manner. Differently configured and positioned vibration apparatus 12, mounting receptacles 90, and/or other features of the system 10 are within the scope of this disclosure. Optionally it may be preferred for the vibration apparatus/housing 80 to be "built into" the body 22 by utilizing a receptacle 90, by way of over molding, and/or in any other suitable manner. For example, the vibration housing 80 can be embedded in the body 22, or more specifically embedded in the at least one sidewall 30, or associated with the cup body 22 in any other suitable manner. As a specific example, FIG. 4 schematically depicts the housing embedded in (e.g., fully or substantially encased in, fully or substantially buried in, and/or fully or substantially enclosed in) the body 22, or more specifically embedded in the at least one sidewall 30 of the body.

Figure 7:
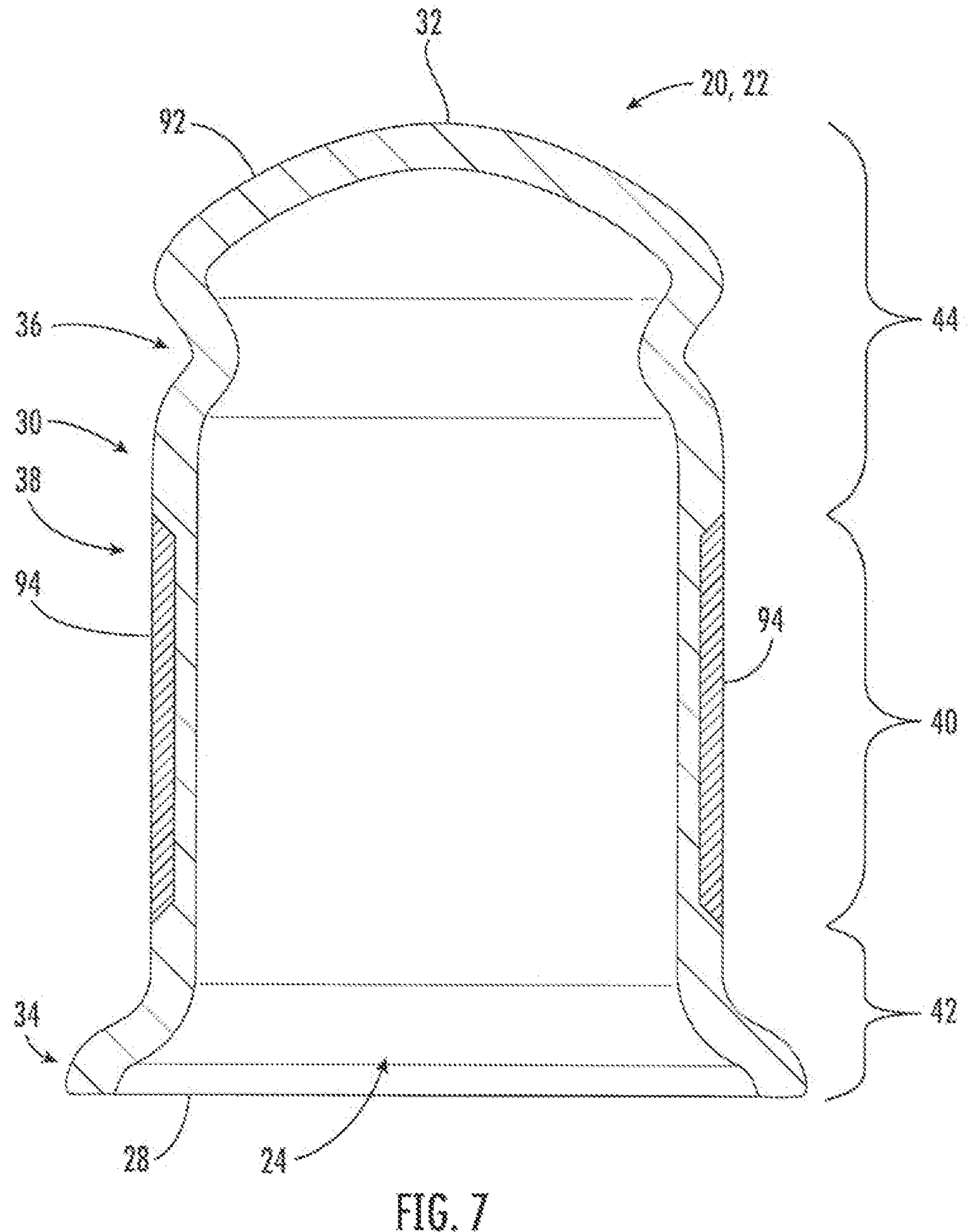
FIG. 7 is another cross-sectional view taken along line 4-4 of FIG. 3, wherein FIG. 7 schematically depicts by way of contrasting cross hatching that the suction cup may be at least partially manufactured, for example, by way of over molding.

Other variations are also within the scope of this disclosure. For example, FIG. 7 is an isolated cross-sectional view similar to FIG. 4 and depicting a container-shaped body 22 in accordance with a version of the first embodiment and/or in accordance with a third embodiment of this disclosure. The first, second, and third embodiments can be alike, except for variations noted and variations that will be apparent to those of ordinary skill in the art.

As an example, the cup body 22 depicted in FIG. 7 can be manufactured using over molding techniques, so that the cup body includes an initially-molded part 92 (e.g., an underlayer that is molded) and an over-molded part 94 (e.g., an overlayer that is molded). In the example depicted in FIG. 7, the initially-molded part 92 can define an annular recess that is filled by the over-molded part 94, so that the annular over-molded part extends completely around the initially-molded part. Alternatively, the one or more over-molded parts 94 can extend partially around the initially-molded part 92.

For forming the initially-molded part 92, a first molding material (e.g., a first silicone molding material) can be directed by way of a port into a first mold cavity corresponding in shape to the at-rest shape of the initially-molded part 92 and then be cross-linked (cured). Then, in a second or modified mold cavity at least partially containing the initially-molded part 92, a second molding material (e.g., a second silicone molding material) can be directed by way of a port into a respective portion of the mold cavity to cover at least a portion (e.g., cover the intermediate portion 40) of the initially-molded part 92 and then be cross-linked (cured) to form the over-molded part 94 extending at least partially (e.g., extending fully or completely) around the initially-molded part.

The first and second molding materials (e.g., silicones and/or other suitable materials) can have different properties such as different hardness and/or stiffness (e.g., different modulus of elasticity). For example, the intermediate portion 40, which includes the over-molded part 94, can be harder and/or stiffer than the portions 42, 44 that do not include the over-molded part. The increased hardness and/or stiffness of the intermediate portion 40 can be attributed, for example, to the use of a second molding material that is harder and/or stiffer (e.g., has a higher modulus of elasticity) than the first molding material and/or to an increased thickness of the intermediate portion 40 caused by the addition of the over-molded part 94.

Figure 8:
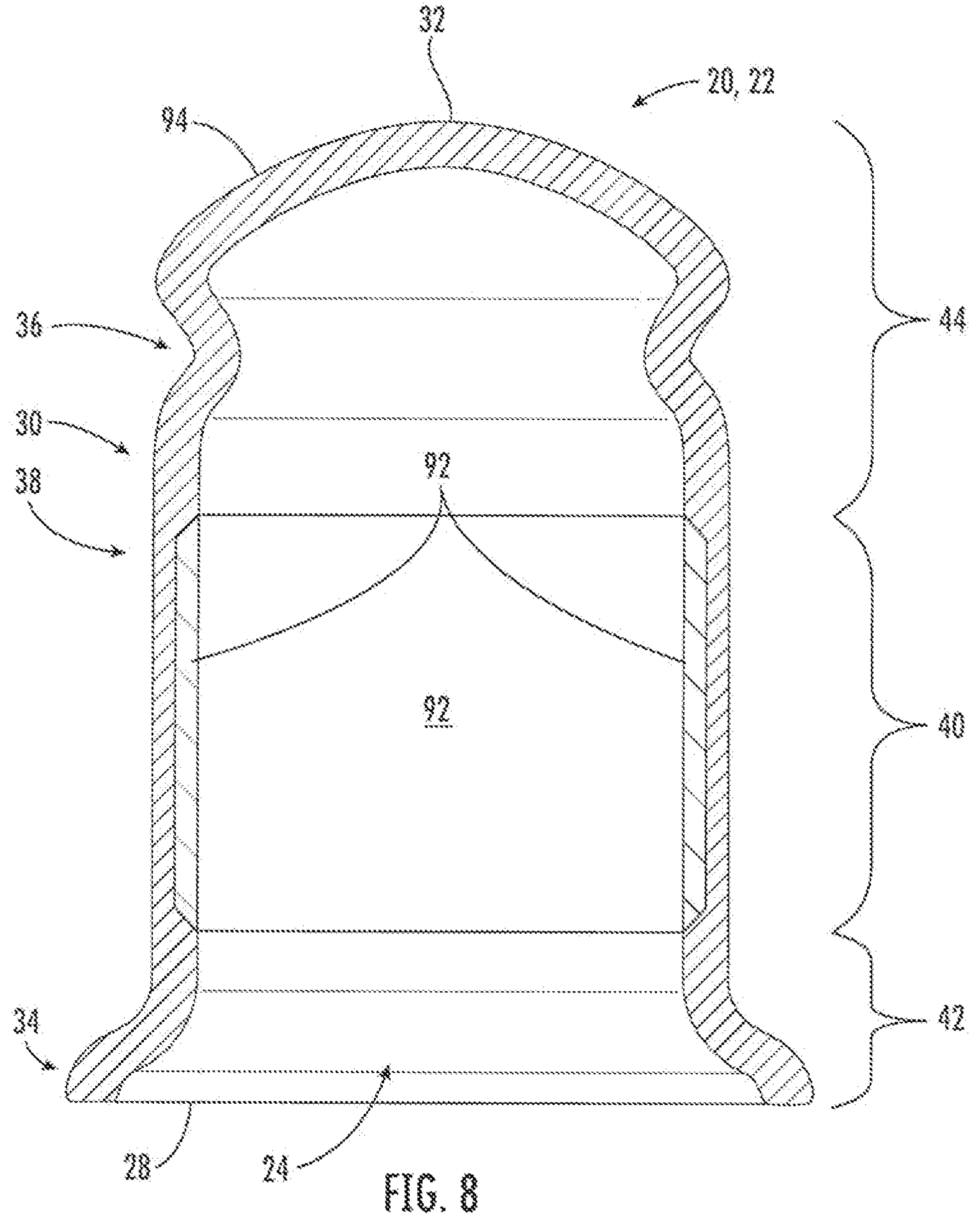
FIG. 8 is further cross-sectional view taken along line 4-4 of FIG. 3, wherein FIG. 8 schematically depicts by way of contrasting cross hatching that the suction cup may be at least partially manufactured, for example, by way of over molding.

Other variations are also within the scope of this disclosure. For example, FIG. 8 is an isolated cross-sectional view similar to FIG. 4 and depicting a container-shaped body 22 in accordance with a version of the first embodiment and/or in accordance with a fourth embodiment of this disclosure. The first, second, and fourth embodiments can be alike, except for variations noted and variations that will be apparent to those of ordinary skill in the art.

As an example, the cup body 22 depicted in FIG. 8 can be manufactured using over molding techniques, so that the cup body includes an initially-molded part 92 (e.g., an underlayer that is molded) and an over-molded part 94 (e.g., an overlayer that is molded). In the example depicted in FIG. 8, the initially-molded part 92 can an annular tube, and the over-molded part 94 can extend completely around the initially-molded part.

For forming the initially-molded part 92, a first molding material (e.g., a first silicone molding material) can be directed by way of a port into a first mold cavity corresponding in shape to the at-rest shape of the initially-molded part 92 and then be cross-linked (cured). Then, in a second or modified mold cavity at least partially containing the initially-molded part 92, a second molding material (e.g., a second silicone molding material) can be directed by way of a port into a respective portion of the mold cavity to cover at least a portion of the initially-molded part 92 and then be cross-linked (cured) to form the over-molded part 94 extending at least partially (e.g., extending fully or completely) around the initially-molded part.

The first and second molding materials (e.g., silicones and/or other suitable materials) can have different properties such as different hardness and/or stiffness (e.g., different modulus of elasticity). For example, the intermediate portion 40, which includes the initially-molded part 92, can be harder and/or stiffer than the portions 42, 44 that do not include the initially-molded part. The relatively high hardness and/or stiffness of the intermediate portion 40 can be attributed, for example, to the use of a first molding material that is harder and/or stiffer (e.g., has a higher modulus of elasticity) than the second molding material and/or to an increased thickness of the intermediate portion 40 caused by its inclusion of the initially-molded part 92.

As another example of variations, differently configured cup bodies 22 are within the scope of this disclosure. For example, whereas some features have been described above as being annular or cylindrical, the sidewall 30 can alternatively be replaced by, or be in the form of, one or more sidewalls configured so that the cup body 22 is shaped differently, such as by being oblong, rectangular, elliptical, more spherical, and/or in any other suitable shape. As another example, the vibration apparatus 12 may be used with a relatively rigid (e.g., glass) cup body having an interior space that is partially evacuated using a vacuum pump.

As further examples, the relatively less flexible or relatively rigid zone(s) (e.g., portion(s)) of the cup body 22 can be provided in a variety of ways. For example, the relatively high rigidity can be provided by embedding (e.g., inserting) one or more articles at predetermined locations in the at least one sidewall 30. The embedded feature(s) may or may not extend around (e.g., encircle) the cup interior space 24. For example, if there is enough of the relatively rigid material embedded in (e.g., buried in) or otherwise associated with the respectively portion of the wall 30 (e.g., silicone wall) the relatively rigid material can make the wall stiff enough without the relatively rigid material completely encircling the cup interior space 24. The embedded features can be pieces of polymeric material (e.g., plastic) and/or other suitable materials. For example, the embedded or other suitable stiffening features can be constructed of any suitable material and be arranged in any suitable patterns. It is believed that the embedded or other suitable stiffening features can be vertical ribs of bamboo, plastic, wood, metal, etc. In the embodiment depicted, for example, in FIGS. 2 and 4, the embedded or other suitable stiffening features can be in or otherwise associated with the intermediate portion 40 between the opposite open and closed end-portions 42, 44, for providing, for example, at least some of the advantageous operational characteristics discussed above.

As further examples and regarding the above-referenced computerized controller that can be contained, for example, by the housing 80 of the vibration apparatus 12, in addition to or alternatively to controlling and/or monitoring the system 10 by way of the user interface and computer features of the housing 80, the system 10 can be at least partially controlled and/or monitored by way of other suitable features. For example, one or more of the suction cups can be controlled and/or monitored remotely by way of wired or wireless (e.g., short-range wireless) communications with other computerized devices (e.g., smartphones; smartwatches; personal digital assistants; portable, tablet, or mobile computers; desktop computers; and/or any other suitable computerized devices). Each suction cup can include sensors and/or other suitable features for sensing, collecting, and relaying information such as battery life, suction pressure, selected program, time left in program or how long the program has been executing, timer/stopwatch functions, and/or any other suitable information. Optionally, a suction cup that can be controlled wirelessly may typically also include local controls in case the wireless controls become inoperable.

Further regarding the above-reference program, by way of executing a software or firmware program, or the like, on one or more of the respective computerized devices, the suction cups can be set to a program which allows them to be controlled together or separately or in preset patterns. The suction cups may be identified by a color or number printed on them, or the like. The suction cups may be of one or multiple sizes and durometers. The size and/or durometer characteristics can be can be distinguished by colors, numbers, and/or the like. For each suction cup, at least some or a majority of it may be clear so that the consumer or professional using the cup can see the skin to which the cup is applied and the color of the skin.

In addition to or alternatively to automatically controlling vibration by way of any one or more of the above-discussed computerized devices, the partial vacuum within the interior space 24 and the resulting suctional force applied to the skin of a user can be automatically controlled and/or monitored by way of any one or more of the above-discussed computerized devices. For example, the suctional force can be automatically adjusted by adjusting the tightness of the strap or band 84 (if present) with a suitable apparatus (e.g., an electromechanical actuator). As another example, the suctional force can be automatically adjusted by any other suitable apparatus (e.g., an electromechanical actuator, vacuum pump, and/or the like) mounted to the cup body 22 (e.g., mounted to the body's closed end-portion 44) and/or in fluid communication with the body's interior space 24.

When the suction cups (e.g., the housing 80) include battery(s), the battery(s) can be recharged with an electrical cord and/or wirelessly. For example, recharging can be accomplished using a charging base that may optionally include its own battery(s), an indicator light configured to indicate when battery(s) are fully charged, and/or any other suitable features.

FIG. 4 schematically depicts an example of the vibration housing 80, or the like, mounted the cup body 22, or more specifically in the at least one wall 30 of the body, although the housing can be mounted in any suitable manner, other examples of which are described above. FIG. 4 further schematically depicts several devices within or otherwise associated with the housing 80, wherein the devices (e.g., at least some electronic components) are schematically designated by numeral 100. The devices 100 can respectively be, for example, at least one battery, at least one electric motor powered by the battery(s), a rotary output shaft of the motor to which an eccentric mass is connected, one or more sensors, electromagnetic signal transmitter(s) and/or receiver(s), and at least one controller.

The at least one controller (see, e.g., 100 of FIG. 4) of the vibration apparatus 20, or the at least one controller associated with the housing 80, can include one or more computers, computer data storage devices, programmable logic devices (PLDs) and/or application-specific integrated circuits (ASIC). A suitable computer can include one or more of each of a central processing unit or processor, computer hardware integrated circuits or memory, user interface, peripheral or equipment interface for interfacing with other electrical components of the system, and/or any other suitable features. The controller(s) can respectively communicate with electrical components of the system by way of suitable signal communication paths (e.g., wired and/or wireless).

Figure 9:
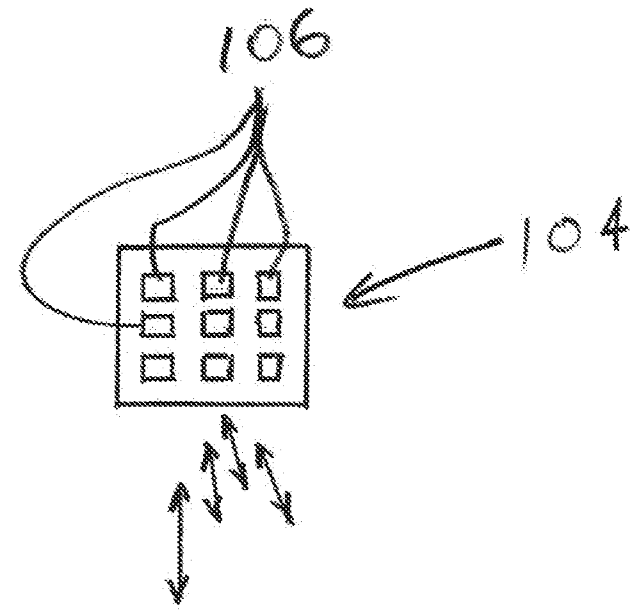
FIG. 9 depicts an example of suction cups of this disclosure arranged in or otherwise associated with a tray or other suitable container, a charging station, and/or the like, wherein the suction cups can be operatively associated with at least one computerized device that can be spaced apart from the suction cups.
Figure 9:
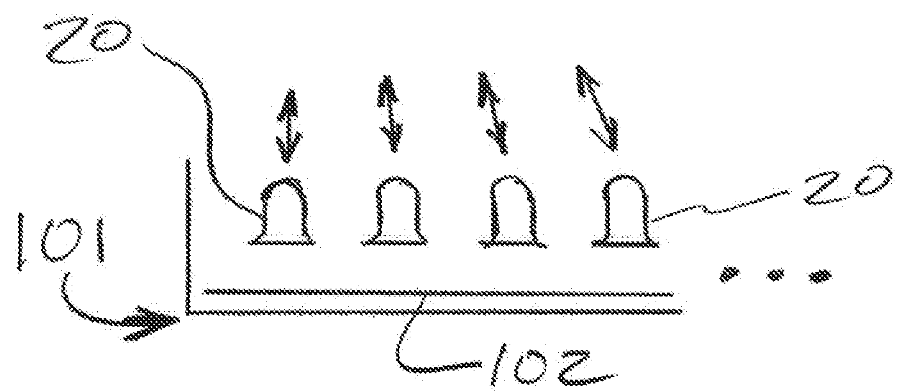

In the example schematically depicted in FIG. 9, one or more of the above-described suction cups 20 with any number of the associated features as described above can be arranged in or otherwise associated with a tray or other suitable container 101 and/or the like (e.g., a charging station). The container or other suitable station 101 can include or be associated with one or more charging ports or one or more conventional charging pads 102 for charging batteries associated with the suction cups 20.

With continued reference to FIG. 9 and at least partially reiterating from above, each suction cup 20 can be operatively associated with at least one "remote" computerized device 104 by way of electrical wires and/wirelessly. Optionally the computerized device 104 can be spaced apart from the suction cups 20. Reiterating from above, the "optionally remote" one or more computerized devices 104 can be, for example, smartphones; smartwatches; personal digital assistants; portable, tablet, or mobile computers; desktop computers; and/or any other suitable computerized devices. The computerized device 104 depicted in FIG. 9 can include or be associated with devices (e.g., at least some electronic components) that are schematically designated by numeral 106. The devices 106 can respectively be, for example, at least one battery, electromagnetic signal transmitter(s) and/or receiver(s), and at least one controller, one or more conventional user interfaces, and/or the like. The at least one controller (see, e.g., 106 of FIG. 9) can include one or more computers, computer data storage devices, programmable logic devices (PLDs) and/or application-specific integrated circuits (ASIC). A suitable computer can include one or more of each of a central processing unit or processor, computer hardware integrated circuits or memory, user interface, peripheral or equipment interface for interfacing with other electrical components of the system, and/or any other suitable features. The controller(s) can respectively communicate with electrical components of the system by way of suitable signal communication paths (e.g., wired and/or wireless).

The one or more suction cups 20 and be monitored, controlled, programmed, reprogrammed, and/or otherwise interacted with by way of their own computerized devices and/or by way of one of more of the "remote" computerized devices 104 that is very close to or numerous feet away from the cups. Electromagnetic communications between the suction cups 20 and the "remote" computerized device 104 are schematically represented by double-ended arrows in FIG. 9.

An example of an aspect of this disclosure is the provision of an improved cup for therapeutic cupping massage that includes both a vibration feature and an enhanced cup design that comprises relatively soft and relatively rigid structural elements.

Another example of an aspect of this disclosure is the provision of a silicone massage cup of any suitable size that can have a rim that is relatively soft and/or relatively less stiff as compared to at least some of or all of a reminder of the body of the cup, wherein the cup can incorporate a rechargeable vibration unit that can be controlled directly by way of manual input and/or can be controlled at least somewhat remotely, for example wirelessly via smartphone or unique computerized tablet, etc.

For example, providing therapeutic cupping massage to a user's body is a way to improve circulation by bringing localized blood flow to the treated area which can provide pain relief, reduce muscle tension and tightness, release scar tissue and fascial adhesions, reduce painful trigger points, and/or promote mobility.

Reiterating from above, it is within the scope of this disclosure for one or more of the terms "substantially," "about," "approximately," and/or the like, to qualify each of the adjectives and adverbs of the foregoing disclosure, for the purpose of providing a broad disclosure. As an example, it is believed that those of ordinary skill in the art will readily understand that, in different implementations of the features of this disclosure, reasonably different engineering tolerances, precision, and/or accuracy may be applicable and suitable for obtaining the desired result. Accordingly, it is believed that those of ordinary skill will readily understand usage herein of the terms such as "substantially," "about," "approximately," and the like. As another example, variations may occur as molds wear and/or are replaced, or the like. Those of ordinary skill in the art will understand that, in such a molding manufacturing process, typically there are engineering tolerances comprising permissible limits in variations of dimensions, and the tolerances can vary in different circumstances. Accordingly, it is believed that those of ordinary skill will readily understand usage herein of the terms such as "substantially," "about," "approximately," and the like.

In the specification and drawings, examples of embodiments have been disclosed. The present invention is not limited to such exemplary embodiments. The use of the term "and/or" includes any and all combinations of one or more of the associated listed items. Unless otherwise noted, specific terms have been used in a generic and descriptive sense and not for purposes of limitation.

The invention claimed is:

1. A suction cup configured for use in cupping therapy, the suction cup comprising:

a body comprising:

at least one sidewall having opposite outer and inner surfaces and extending at least partially around an interior space, wherein the outer surface of the at least one sidewall defines at least a portion of an exterior surface of the body, the inner surface of the at least one sidewall is positioned between the exterior surface of the body and the interior space, and the inner surface defines at least a portion of an interior surface of the body that is contiguous with the interior space, opposite end portions at least partially defined by the at least one sidewall and comprising an open end-portion and a closed end-portion, the open end-portion comprising at least one rim extending around an opening to the interior space, and an intermediate portion at least partially defined by the at least one sidewall, wherein the intermediate portion is positioned between the opposite end portions and spaced apart from the rim;

at least a portion of the body being elastic and configured so that the body is:

capable of being squeezed to transition the body from an at-rest configuration to a partially-collapsed configuration, and elastically biased toward the at-rest configuration;

a volume of the interior space being greater in the at-rest configuration than in the partially-collapsed configuration;

each of the rim and the closed end-portion being less stiff than the intermediate portion;

the intermediate portion comprising an overlayer adjacent an underlayer;

the overlayer extending at least partially around the interior space and defining at least a portion of the exterior surface of the body;

the underlayer comprising a polymeric elastomer and extending at least partially around the interior space and defining at least a portion of the interior surface of the intermediate portion of the body that is contiguous with the interior space;

all of the underlayer is spaced apart from the rim extending around the opening to the interior space; and at least some material of the overlayer and/or the underlayer that is spaced apart from the rim having a higher modulus of elasticity than material of the rim and material of the closed end-portion of the body.

2. The suction cup according to claim 1, further comprising an electrically rechargeable vibration unit that is operatively associated with the intermediate portion of the body to cause at least the open end-portion of the body to vibrate.

3. The suction cup according to claim 2, wherein the vibration unit includes a user interface for being manually controlled.

4. The suction cup according to claim 2, wherein the vibration unit is configured to communicate with, and be at least partially controlled by, a remote computer device.

5. The suction cup according to claim 1, wherein:

the overlayer is molded to the underlayer; and the overlayer molded to the underlayer extends completely around the interior space.

6. The suction cup according to claim 1, wherein:

the underlayer is molded to the overlayer; and the underlayer molded to the overlayer extends completely around the interior space.

7. The suction cup according to claim 1, wherein:

the overlayer comprises a detachable strap mounted to the underlayer and extending at least partially around the body.

8. The suction cup according to claim 7 in combination with a vibration apparatus, wherein the vibration apparatus is mounted to the strap and configured to at least partially cause vibrational motion of the rim.

9. The suction cup according to claim 7, wherein each of the strap, the intermediate portion, the open end-portion, and the closed end-portion comprises an elastomeric material.

10. The suction cup according to claim 9, wherein the elastomeric material of the intermediate portion, the open end-portion and the closed end-portion have about the same modulus of elasticity; and the elastomeric material of the strap has a higher modulus of elasticity than the elastomeric material of the intermediate portion, the open end-portion and the closed end-portion.

11. The suction cup according to claim 9, wherein the intermediate portion, the open end-portion and the closed end-portion are formed of the same elastomeric material.

12. The suction cup according to claim 1 in combination with a vibration apparatus, wherein:

the vibration apparatus is mounted to the intermediate portion and is spaced apart from the rim; and the vibration apparatus is configured to at least partially cause vibrational motion of the rim.

13. The suction cup according to claim 1, wherein one or more of the intermediate portion, the open end-portion, and the closed end-portion comprise an elastomeric material.

14. The suction cup according to claim 1, wherein two or more of the intermediate portion, the open end-portion, and the closed end-portion are colored differently from one another to identify variations in stiffness of the intermediate portion, the open end-portion, and/or the closed end-portion.

15. The suction cup according to claim 1, wherein each of the intermediate portion, the open end-portion, and the closed end-portion comprises an elastomeric material.

16. The suction cup according to claim 15, wherein:

the elastomeric material of the open end-portion and the elastomeric material of the closed end-portion have about the same modulus of elasticity.

17. The suction cup according to claim 16, wherein the elastomeric material of each of the intermediate portion, the open end-portion, and the closed end-portion comprises silicone.

18. The suction cup according to claim 1, wherein:

the intermediate portion, the open end-portion and the closed end-portion are fabricated as a unitary article.

19. The suction cup according to claim 1, wherein the body comprises a transparent portion.

20. The suction cup according to claim 1, wherein the body comprises contrasting colored portions.

21. The suction cup according to claim 1, wherein the body comprises one or more visual indicators to aid a user of the suction cup.

22. The suction cup according to claim 1, wherein the overlayer comprises a detachable strap mounted to the underlayer and extending completely around the body.

23. The suction cup according to claim 1, wherein:

the overlayer comprises a band mounted to the underlayer and extending at least partially around the body.

24. The suction cup according to claim 23, wherein the overlayer comprises the band mounted to the underlayer and extending completely around the body.

25. The suction cup according to claim 1, comprising a vibration apparatus comprising an electromechanical vibrator mounted to the intermediate portion of the body of the suction cup, wherein:

the overlayer comprises a band mounted to the underlayer and extending at least partially around the suction cup;

the vibration apparatus is configured to at least partially cause vibrational motion of at least the intermediate portion, the open end-portion, and/or the closed end-portion of the body; and the intermediate portion of the body of the suction cup together with the vibration apparatus is stiffer than the open end-portion and the closed end-portion of the body of the suction cup.

26. The suction cup according to claim 25, wherein the electromechanical vibrator is positioned at least partially in a receptacle of the suction cup.

27. The suction cup according to claim 25, wherein the band is positioned at least partially in a receptacle of the suction cup.

28. The suction cup according to claim 25, wherein the overlayer comprises the band mounted to the underlayer and extending completely around the body.

* * * * *